United States Patent
Eichhorn et al.

(10) Patent No.: US 8,850,897 B2
(45) Date of Patent: Oct. 7, 2014

(54) ELECTRICALLY CONDUCTIVE NANOTUBE COMPOSITE SENSOR FOR MEDICAL APPLICATION

(75) Inventors: Wade R. Eichhorn, Minneapolis, MN (US); Kristian G. Wyrobek, Minneapolis, MN (US)

(73) Assignee: 7-Sigma Incorporated, Minneapolis, MN (US)

( * ) Notice: Subject to any disclaimer, the term of this patent is extended or adjusted under 35 U.S.C. 154(b) by 323 days.

(21) Appl. No.: 13/397,737

(22) Filed: Feb. 16, 2012

(65) Prior Publication Data
US 2013/0218050 A1    Aug. 22, 2013

(51) Int. Cl.
*G01B 7/16*    (2006.01)

(52) U.S. Cl.
USPC .............................................. 73/774; 73/777

(58) Field of Classification Search
CPC ............................. C01B 31/022; G01L 9/0035
USPC ................. 73/774–777, 760; 72/777
See application file for complete search history.

(56) References Cited

U.S. PATENT DOCUMENTS

| | | | | |
|---|---|---|---|---|
| 7,453,085 B2* | 11/2008 | Chang et al. | ..................... | 257/41 |
| 7,598,723 B2* | 10/2009 | Gaillard et al. | ............ | 324/76.42 |
| 7,645,497 B2* | 1/2010 | Spath et al. | ..................... | 428/1.4 |
| 7,730,547 B2 | 6/2010 | Barrera | | |
| 8,132,468 B2* | 3/2012 | Radivojevic | .................... | 73/777 |
| 8,492,755 B2* | 7/2013 | Hu et al. | ........................ | 257/40 |
| 8,495,917 B2* | 7/2013 | Radivojevic | .................... | 73/777 |
| 8,587,422 B2* | 11/2013 | Andrews et al. | .............. | 340/438 |
| 2008/0129278 A1* | 6/2008 | Dai et al. | ....................... | 324/109 |
| 2008/0238882 A1* | 10/2008 | Sivarajan et al. | ............. | 345/174 |
| 2009/0293631 A1 | 12/2009 | Radivojevic | | |
| 2009/0308742 A1 | 12/2009 | Paranjape | | |
| 2011/0148815 A1* | 6/2011 | Tsai | .............................. | 345/175 |
| 2011/0275502 A1 | 11/2011 | Eichhorn | | |
| 2011/0306824 A1 | 12/2011 | Perron | | |
| 2011/0316522 A1 | 12/2011 | Shinobu | | |
| 2011/0319755 A1 | 12/2011 | Stein | | |

OTHER PUBLICATIONS www.mech.northwestern.edu/FOM/LiuCh06v3_072505.pdf ; printed on May 7, 2012.
"A carbon nanotube/polymer strain sensor with linear and anti-symmetric piezoresistivity," Gang Yin et al. Published online before print Apr. 26, 2011, doi: 10.1177/0021998310393296 Journal of Composite Materials Jun. 2011 vol. 45 No. 12 1315-1323.

(Continued)

*Primary Examiner* — Max Noori
(74) *Attorney, Agent, or Firm* — Mark A. Litman & Associates, P.A.

(57) ABSTRACT

A sensor and method of sensing dimensional changes, stress changes or pressure changes on a substrate uses a sensor in the following manner. Temporarily and non-destructively attach a piezoresistant sensor to a surface. The piezoresistant sensor has an electrically conductive elastic body having at least one pair of opposed ends, and the elastic body contains conductive nanotubes homogeneously distributed therein. The elastic body has at least one surface with two opposed ends and electrodes at each of the opposed ends. A current is passed through the elastic body between the two electrodes. The current passing through the elastic body is sensed (e.g., a voltmeter). A mechanical step is performed with or on the substrate, and the sensor measures changes in the current between the electrodes, indicating strain or pressure on the sensor.

9 Claims, 9 Drawing Sheets

(56) References Cited

OTHER PUBLICATIONS

"Flexible Strain Sensor Based on Carbon Nanotube Rubber Composites," Jin-Ho Kim et al., Nanosensors, Biosensors and Info-Tech Sensors and Systems 2010, edited by Vijay K. Varadan, Proc. Of SPIE vol. 7646, 7646ON.

"Piezoresistive response of epoxy composites with carbon nanoparticles under tenssile load," Wichmann, Malte H.G., et al., Physical Review b80, 245437 (2009, The American Physical Society.

"Supersensitive linear piezoresistive property in carbon nanotubes/silicone rubber nanocomposites," Zhi-Min Dang et al., Journal of Applied Phyisics, 104, 024114 (2008), American Institute of Physics.

Bozovic, Delores et. al., Plastic Deformations in Mechanically Strained Single-Walled Carbon Nanotubes, Department of Physics and Chemistry and Chemical Biology, Harvard University, Cambridge, MA 02138 (16 Pages).

Dolores Bozovic et al., Plastic Deformations in Mechanically Strained Single-Walled Carbon Nanotubes, Department of Physics, Harvard University, Cambridge, MA 02138, Department of Chemistry and Chemical Biology, Harvard University, Cambridge, MA 02138.

\* cited by examiner

Carbon Nanotube LIM Silicone Physical Properties
0.5%, 1%, 2% Loading of Multiwall Carbon Nanotubes

| Parameter | Plain LIM | 0.5% of CNT | 1% of CNT | 2% of CNT |
|---|---|---|---|---|
| Max. Torque, lb-in | 5.73 | 6.01 | 6.61 | 9.14 |
| TC90, Sec | 0.17 | 0.13 | 0.20 | 0.15 |
| Hardness, Shore A | 38 | 40 | 43 | 43 |
| Tensile, psi | 365 | 335 | 392 | 449 |
| Elongation, % | 256 | 227 | 230 | 265 |
| Modulus, psi | 168 | 160 | 197 | 220 |
| Tear, ppi | 30.4 | 28.6 | 41 | 52 |
| Sp.Gr | 1.255 | 1.31 | 1.31 | 1.284 |
| Compression set, % 22 hrs @ 350°f | 2.0 | 3.2 | 7.0 | 12.5 |
| Volume change in silicone oil,% 22hrs @ 350°F | 34 | 43 | 35 | 35 |
| Electrical resistivity, Ohm.cm | $10^{13}$ | $5 \times 10^4$ | $1.3 \times 10^3$ | Out of range, too low |

Fig. 1

ELECTRICALLY CONDUCTIVE NANOTUBE COMPOSITE SENSOR FOR MEDICAL APPLICATION

BACKGROUND OF THE INVENTION

1. Field of Invention

The present invention relates to the field of sensors, particularly sensors that indicate local changes in conditions on articles, and more particularly in the field of positionable sensors that can be applied to a surface, used in a sensing procedure, and then removed from the surface. The invention also relates to flexible electrical sensors for use in medical applications to provide information or measurement on the stress, elongation, pressure, or load that is applied to or placed upon the sensor. The present invention may be utilized as part of a medical device system to provide information or measurement of stress, elongation, pressure, or load in the insertion process or the performance of the medical device system.

2. Background of the Art

Piezoresistivity, the change in electrical resistivity under stress or strain, may be a property of electrical conductive materials, as is with electrically conductive rubbers containing conducting nanotubes such as single-wall or multi-wall carbon nanotubes. The piezoresistive effect describe the changing resistivity of a semiconductor due to applied mechanical stress. The piezoresistive effect differs from the piezoelectric effect. In contrast to the piezoelectric effect, the piezoresistive effect only causes a change in electrical resistance; it does not produce an electric potential. Piezoresistivity is defined by $$\rho_\sigma = \frac{\left(\frac{\partial \rho}{\rho}\right)}{\varepsilon}$$

Where
∂ρ=Change in resistivity
ρ=Original resistivity
ε=Strains

When a voltage is applied to such a material, and stress or strain is applied to the material, the electrical resistance of the material changes in response to the stress, and the resulting change in resistance can be measured in the change in current through the material. Applying a constant voltage to a conductive nanotube flexible polymer composite and monitoring the output current of the conductive composite while a stress or strain is applied, gives a direct mathematical correlation between the change in resistivity caused by the forces applied and the change in local dimensions of the article formed by the material. Flexibility of nanotube rubber composite, as well as the large change in resistivity associated with an electrically conductive nanotube composite, has an advantage over piezoelectric sensors, especially over large numbers of deformations. The electrically conductive nanotube rubber composite also has advantages over electrically capacitive sensors due to the relatively large change in resistivity is well above the back ground electrical noise level, thus potentially better suited for environments where the electrical signal to noise ratio may be a challenging problem for capacitive sensors.

U.S. Patent Application Publication No. 20110319755 (Stein) describes a sensing insert device for measuring a parameter of the muscular-skeletal system. The sensing insert device can be temporary or permanent. The sensing module is a self-contained encapsulated measurement device having at least one contacting surface that couples to the muscular-skeletal system. The sensing module comprises one or more sensing assemblages, electronic circuitry, an antenna, and communication circuitry. The sensing assemblages are between a top plate and a bottom plate in a sensing platform. The bottom plate is supported by a ledge on an interior surface of a sidewall of a housing. A cap couples to top plate. The cap is adhesively coupled to the housing. The adhesive is flexible allowing movement of the cap when a force, pressure, or load is applied thereto.

U.S. Patent Application Publication No. 20110316522 (Shinobu) provides a sensing device that holds a piezoelectric sensor and a channel forming member placed on the sensor in a closely contacted state while maintaining a shape of space of a passage space formed inside the device. In a sensing device that senses a substance to be sensed based on a variation in an oscillation frequency caused by an absorption of the substance to be sensed in an absorption layer provided on a piezoelectric resonator of a piezoelectric sensor, a holding member holds the piezoelectric sensor and a channel forming member that forms a passage space through which a sample fluid passes on an upper surface side of the sensor, in a vertically stacked state. A cover member is placed on the channel forming member, and a pressing part which is raised/lowered by a first raising/lowering mechanism presses the cover member 1510 placed on the channel forming member downward with a previously set force.

U.S. Patent Application Publication No. 20110306824 (Perron) describes an implantable system comprises a housing that includes a flexible reservoir and a piezoelectric sensor system. The flexible reservoir is coupled to an inflatable portion of a gastric band via a fluid inlet/outlet. The flexible reservoir contains a fluid and has an expanded configuration and a contracted configuration. An access port may be coupled to the flexible reservoir and/or the gastric band to facilitate filling and draining the reservoir and/or the gastric band. A movable wall is slidably positioned around the flexible reservoir to move the flexible reservoir between the expanded configuration and the contracted configuration to move the fluid into and out of the inflatable portion of the gastric band. A driving mechanism is positioned around the movable wall and is capable of changing the size of the movable wall to compress or expand the flexible reservoir. A motor, coupled to the driving mechanism, may actuate the driving mechanism.

U.S. Patent Application Publication No. 20090293631 (Radivojevic) describes a sensing device for measuring flexural deformations of a surface. Such a sensing device may be used as a user interface in portable electronic devices. The sensing device comprises at least one cell. The cell comprises a first electrode, a central electrode, a second electrode, a first piezoelectric sensing layer placed between the first electrode and the central electrode, a second piezoelectric sensing layer placed between the central electrode and the second electrode, and a circuit connected to the first, second and the central electrodes. The circuit is configured to measure a first electrical signal between the first electrode and the central electrode, and a second electrical signal between the second electrode and the central electrode. At least one of the first electrical signal and the second electrical signal is responsive to an external stress applied on the sensing device.

U.S. Patent Application Publication No. 20090308742 (Paranjape) relates to a system and method that co-locates in a small flexible, configurable system and multi-level substrate sampling, rapid analysis, bio-sample storage and delivery functions to be performed on living tissues or matter obtained from living organisms. The types of the sampling may include chemical, biochemical, biological, thermal, mechanical, electrical, magnetic and optical, sampling. In general, the analysis performed at the point of sampling measures the sample taken and records its value. The bio-sample storage function encapsulates a small sample of analyte and preserves it for subsequent examination or analysis, either on the organism by the system or at a remote location by an independent analysis system. Once stored, the sample can provide a record of a biological state at the precise time of sampling. The delivery at the point of sampling can include chemical, biochemical, thermal, mechanical, electrical, magnetic and optical stimuli.

U.S. Pat. No. 7,730,547 (Barrera) is directed toward devices comprising carbon nanotubes that are capable of detecting displacement, impact, stress, and/or strain in materials, methods of making such devices, methods for sensing/detecting/monitoring displacement, impact, stress, and/or strain via carbon nanotubes, and various applications for such methods and devices. The devices and methods of the present invention all rely on mechanically-induced electronic perturbations within the carbon nanotubes to detect and quantify such stress/strain. Such detection and quantification can rely on techniques which include, but are not limited to, electrical conductivity/conductance and/or resistivity/resistance detection/measurements, thermal conductivity detection/measurements, electroluminescence detection/measurements, photoluminescence detection/measurements, and combinations thereof. All such techniques rely on an understanding of how such properties change in response to mechanical stress and/or strain.

U.S. Patent Application Publication No. 20090308742 20110275502 (Eichhorn) discloses an electrically conductive roller, belt or mat for an elastomeric printing surface. The elastomeric material may be comprised of a selection of base rubber materials chosen from silicone, ethylenic elastomers and rubbers such as ethylene propylene diene monomer based elastomers, or class-M rubbers (EPDM), FKM (fluorocarbon or perfluorcarbon polymers.elastomers and rubbers, especially fluorelastomers as defined in ASTM D1418), polyurethanes and other elastomeric rubber polymers to which nanotubes are added to form a nanotube rubber composite. Specifically, the electrically conductive roller, belt or mat elastomeric material composition is comprised of a carbon nanotube silicone rubber utilizing a platinum cured liquid silicone rubber with very small loadings of carbon nanotubes. The patent application describes the carbon nanotube composite material physical & electrical properties as applied to the printing component and various embodiments including carbon nanotube composites bonded to other materials such as metals and thermoplastics.

The M class includes rubbers having a saturated chain of the polymethylene type. Dienes currently used in the manufacture of EPDM rubbers are dicyclopentadiene (DCPD), ethylidene norbornene (ENB), and vinyl norbornene (VNB). The ethylene content is around 45% to 75%. The higher the ethylene content the higher the loading possibilities of the polymer, better mixing and extrusion. Peroxide curing these polymers give a higher crosslink density compared with their amorphous counterpart. The amorphous polymers are also excellent in processing. This is very much influenced by their molecular structure. The dienes, typically comprising from 2.5% up to 12% by weight of the composition, serve as crosslonks when curing with sulphur and resin, with peroxide cures the diene (or third monomer) functions as a coagent, which provide resistance to unwanted tackiness, creep or flow during end use.

Significant background technology on piezeresistance in sensors is provided at www.mech.northwestern.edu/FOM/LiuCh06v3_072505.pdf (which is submitted with this application).

"A carbon nanotube/polymer strain sensor with linear and anti-symmetric piezoresistivity," Gang Yin et al. Published online before print Apr. 26, 2011, doi: 10.1177/0021998310393296 Journal of Composite Materials June 2011 vol. 45 no. 12 1315-1323 describes improved piezoresistive sensors in the aerospace industry. Additional Journal disclosures in this area of technology include "Flexible Strain Sensor Based on Carbon Nanotube Rubber Composites," Jin-Ho Kim et al., Nanosensors, Biosensors and Info-Tech Sensors and Systems 2010, edited by Vijay K. Varadan, Proc. Of SPIE Vol. 7646, 7646ON; "Piezoresistive response of epoxy composites with carbon nanoparticles under tensile load," Wichmann, Malte H. G., et al., *PHYSICAL REVIEW* b80, 245437 (2009, THE American Physical Society; "Supersensitive linear piezoresistive property in carbon nanotubes/silicone rubber nanocomposites," Zhi-Min Dang et al., *Journal of Applied Physics*, 104, 024114 (2008), American Institute of Physics.

All of the references cited herein are incorporated by reference in their entirety. It is desirable to find additional utility for sensors in the manufacturing and medical fields.

SUMMARY OF THE INVENTION

A flexible strip of elastomeric polymer containing from 0.02 to 8% by total weight of conductive nanotubes provides a useful piezoresistive sensor. These sensors may be removably attached to surfaces during handling, and measurements may be taken of changes in resistivity (e.g., by measuring low voltage current across the strip) to determine changes in dimensions, stress and pressure on the strip. By having relatively secure, though temporary attachment to the surface of an article, changes in the dimensions, pressure and stress on the article may be estimated with a significant degree of assurance of meaningful results.

BRIEF DESCRIPTION OF THE FIGURES

FIG. 1 is a table of physical properties of carbon nanotube liquid silicone rubber composites samples used for a roller, belt or mat base elastomeric polymer according to the invention.

DETAILED DESCRIPTION OF THE INVENTION

Figure 2:
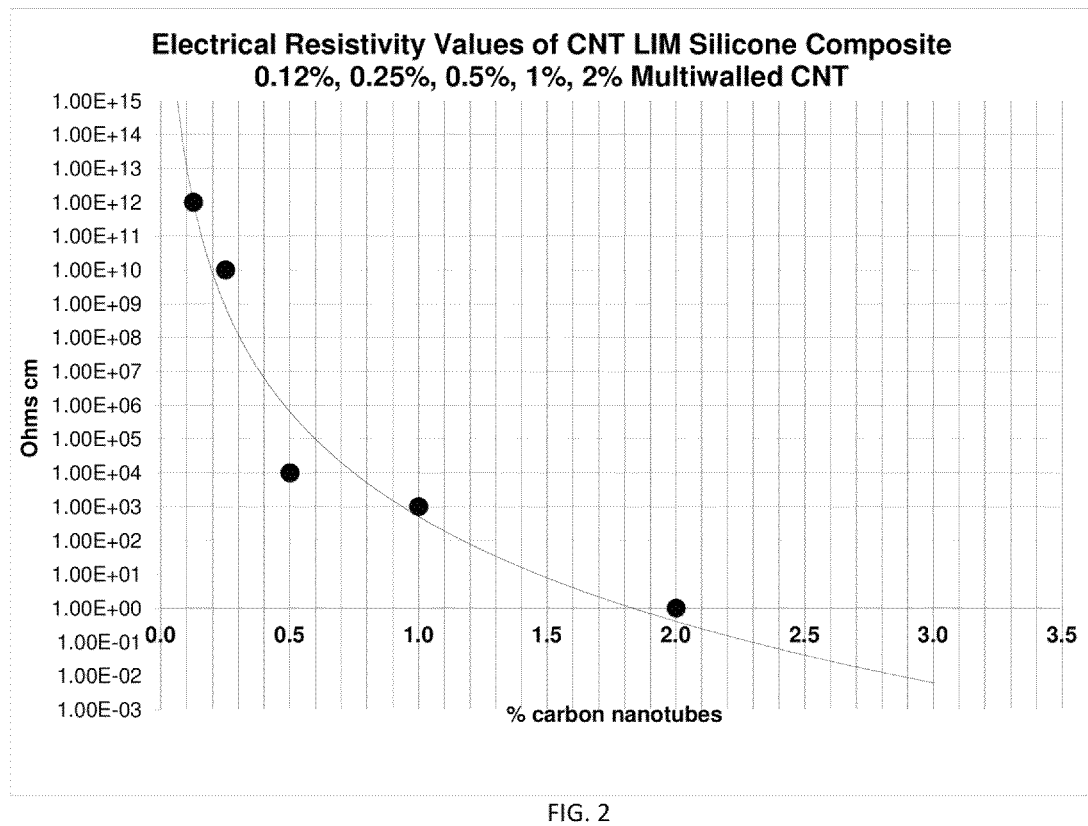
FIG. 2 is a graph of the electrical resistivity property of carbon nanotube liquid silicone composites used for a roller, belt or mat base elastomeric polymer according to the invention.

The following definitions and descriptions are useful in understanding the scope of technology used in the practice of the present technology.

Nanocomposite Definition:

Nanomaterials that combine one or more separate components in order to obtain the best properties of each component (composite). In nanocomposite, nanoparticles (clay, metal, carbon nanotubes) act as fillers in a matrix, usually polymer matrix.

Nanomaterials Definition:

Nanomaterials can be defined as materials which have structured components with at least one dimension less than 100 nm. Materials that have one dimension in the nanoscale are layers, such as a thin films or surface coatings. Some of the features on computer chips come in this category. Materials that are nanoscale in two dimensions include nanowires and nanotubes. Materials that are nanoscale in three dimensions are particles, for example precipitates, colloids and quantum dots (tiny particles of semiconductor materials). Nanocrystalline materials, made up of nanometer-sized grains, also fall into this category. Preferred dimensions for nanotubes are diameters of from 3 Angstroms, preferably at least 5 Angstroms, more preferably at least 10 Angstroms up to 100 nm, preferably up to 70 nm, more preferably up to 50 nm. Preferred ranges of diameters for nanotubes according to the present invention are from 0.5 nm to 30 nm.

Nanometer Definition:

One nanometer (nm) is equal to one-billionth of a meter, $10^{-9}$ m. Atoms are below a nanometer in size, whereas many molecules, including some proteins, range from a nanometer upwards.

Nanoparticle Definition:

Nanoparticles are particles of less than 100 nm in diameter. The preferred size range for diameters of nanotubes described above tends to be a preferred range for the largest dimension of nanoparticles also.

Nanotube Definition (Carbon Nanotubes):

Carbon nanotubes (CNTs) were discovered by Sumio Iijima in 1991. Carbon nanotubes are generally fullerene-related structures which consist of rolled graphene sheets, although multiple molecular level structures of nanotubes and variations in structure have been created and described. There are two generic types of CNT: single-walled (one tube) or multi-walled (more tubes). Both of these are typically a few nanometers in diameter and several micrometers to centimeters long.

Nanowires Definition:

Nanowires are ultrafine wires or linear arrays of dots, made from a wide range of materials, with nanodimension diameters. These are essentially extremely long nanotubes in some instances.

Elastomeric Polymers

Elastomers are usually thermoset resins (requiring crosslinking or vulcanization) but may also be thermoplastic polymers. The polymer chains are cross-linked during curing, i.e., vulcanizing. The molecular structure of elastomers can be imagined as a 'spaghetti and meatball' structure, with the meatballs signifying cross-links. The elasticity is derived from the ability of the long chains to reconfigure themselves to distribute an applied stress. The covalent cross-linkages ensure that the elastomer will return to its original configuration when the stress is removed. As a result of this extreme flexibility, elastomers can reversibly extend (that is, retain their elasticity at least once, and preferably repeatedly without inelastic deformation occurring) from 5-700%, depending on the specific material. Without the cross-linkages or with short, uneasily reconfigured chains, the applied stress would more likely result in a permanent deformation.

Temperature effects are also present in the demonstrated elasticity of a polymer. Elastomers that have cooled to a glassy or crystalline phase will have less mobile chains, and consequentially less elasticity, than those manipulated at temperatures higher than the glass transition temperature of the polymer. It is also possible for a polymer to exhibit elasticity that is not due to covalent cross-links. For example, crystalline polymers can be treated to alter their short range versus long range crystalline morphology to alter the elastic properties as well as other physical properties.

Underlying technology within the scope of the present invention includes both sensors and methods of using sensors in processes or procedures. The novel articles used as sensors in the practice of the present technology comprise millimeter dimension (diameters and or three major dimensions between 0.2 to 100 mm) polymeric structures comprising from 0.2% to 8% by total weight of conductive nanotubes. The articles must have some degree of elastic deformation properties such that in at least one dimension (e.g., the length of a nanotube) there can be at least 5% total elastic deformation from a base line 0 stress article with a return to that base line 0 stress (unstressed) length that has not inelastically changed by more than 0.5%. When used, the articles must have electrodes attached across the conductive dimension of the article, preferably aligned with the dimension of expected stress and elongation. Although the electrodes may be separated so as to extend perpendicularly or acutely or obtusely with respect to the expected dimension of elongation and stress, the piezoresistive effect is more accurately measured along a single dimension (or possibly along multiple directions, as the nanotubes often are not uniformly aligned, but may curl and twist into three dimensional form) parallel with the stress and elongation. The article may have electrodes fixed into the structure or may have attachment points for attaching the electrodes and placing them into contact with the conductive layer. The electrodes would extend to and be in electrical communication connection with a current or voltage measuring system. A voltage is applied across the conductive layer (the polymer-containing nanotubes) in the sensor, which may again be parallel with, perpendicular to or angled with respect to at least one dimension along which stress and elongation is expected during use, and the changes in the current (and/or voltage) is measured and the changes are correlated to stress and/or percentages of elongation in the article. As the current passed between sensors will change in a repeatable manner no matter what the orientation between the current flow and the elongation/pressure may be, a look-up table or other correspondence between the elongation/strain/pressure and changes in current can be established as a reference.

The article, such as an elongate tube or strip or patch, is temporarily secured to a surface that is to be manipulated or mechanically processed or chemically processed, where such processing or handling has surrounding concerns about changes in stress, dimensions, pressure or the like that can be measured by piezoresistive measurements. The removable attachment could be by any means that will secure the sensor article with sufficient force to the substrate or surface so that all degrees of expected stress and dimensional change can be endured, with the sensor article during and throughout the application of stress. The securing should be reversible, that is the article should be removable from the surface without substantive damage to the surface. This can be accomplished by mechanical fasteners (e.g., clips, posts, snaps, pins, hooks, and the like) or by pseudo-chemical attachment through adhesives (e.g., solvent soluble adhesives that can be washed away by solvents, including water, for example; thermal adhesives that can be attached by heating and softened for removal by heating). Where a surface has a natural porosity to it, enabling physical attachment, such as a fabric or mesh substrate, as in reinforcing mesh used in medical practices, such as pelvic support and pelvic health, shoulder health, knee help, ankle health, neck health, internal organ health and the like. An elongate element, such as a sensor tube for example, may be a conductive nanotube-containing polymer of from 0.2 to 10 mm in diameter, and from 2 to 100 mm in length. A patch may comprise a square or rectangular OR oval or other geometric shape flat material comprising a conductive nanotube-containing polymer and two opposed edges. The electrodes are positioned at or about the opposed edges, the current is passed through the polymer, stress is applied to the patch (directly or through coincident stress on the surface to which the patch is removably attached), and the change in current is measured and correlated with amounts of stress and/or dimensional changes.

Various aspects of the invention include a piezoresistive sensor having an electrically conductive elastic body having at least one pair of opposed ends, and the elastic body containing conductive nanotubes homogeneously distributed therein, the elastic body having at least one surface with physical attaching elements thereon and the elastic body having electrodes attached at each of the at opposed ends. The conductive elastic body (that is the actual body of the sensor made from a composition) has an elastic range of between about 5% elongation and about 500% elongation. The conductive elastic body may have for example, from about 0.02% to 8% by total weight of the elastic body (not including electrodes) of conductive nanotubes. Preferably the conductive nanotubes are from about 0.2 to 5% by total weight of the conductive elastic body. The conductive nanotubes may be carbon nanotubes. The elastic body may be a polymer as described herein. The polymer may, by way of non-limiting examples, be selected from the group consisting of epoxy resins, silicone resins, ethylenically unsaturated elastomeric resins, and natural rubbers. The physical attaching elements are selected from the group consisting of pins, posts, hooks and snaps, as well as the other temporary securing mechanisms described herein.

The present technology also includes a method of sensing dimensional changes, stress changes or pressure changes on a substrate including steps (not necessarily in the following order) of: temporarily and non-destructively attaching a piezoresistant sensor to a surface, the piezoresistant sensor comprising an electrically conductive elastic body having at least one pair of opposed ends, and the elastic body containing conductive nanotubes homogeneously distributed therein, the elastic body having at least one surface with two opposed ends and electrodes at each of the opposed ends, passing a current through the elastic body between the two electrodes, sensing the current passing through the elastic body, performing a mechanical step on the substrate, and measuring changes in the current between the electrodes. The measured changes are identified by an electronic look-up table or other execution of software by a processor receiving information/signals of the changes to identify changes in properties or conditions that are being monitored. The information may then be displayed on a video monitor if desired. The measured changes in current between the electrodes is related by execution of code in a processor to a pressure, stress level or change in dimension during performing of the mechanical step. After measured changes in current have been identified, the sensor may be or is from the substrate. The sensor may again, in this process, be attached to the substrate by hooks, pins or post grasping a mesh surface of the substrate.

The invention also relates to a flexible electrically sensor for use in pelvic health applications to provide information or measurement on the stress, elongation, pressure, or load that is applied to a surgical mesh medical device during the insertion process of a prolapse organ medical procedure. During pelvic organ prolapse, the internal structures that support the pelvic organs such as the bladder, uterus, and bowel drop from their normal position and "prolapse" into the vagina. Pelvic organ prolapse surgery can also be performed through the abdomen or vagina with stitches or surgical mesh to reinforce the repair and correct the anatomy.

In one preferred embodiment of this method, the substrate is a mesh to support tissue, and the mechanical step performed is planting the mesh into a patient to support tissue. The mesh may be able to undergo displacement or redistribution of elongated elements such as fibers, filaments, cable, wires and the like in the mesh that are not elastic (e.g., they shift under pressure), yet are not inelastic) that is, the elongated elements do not stretch inelastically, but shift out of position so their original placement and/or alignment has changed.

The following description of the Figures will further assist in an understanding of the present technology.

FIG. 1 is a table showing a graphic representation of date relating physical properties of carbon nanotube silicone rubber composites within the generic scope of the present invention. The table shows those properties of materials composed of a base-platinum-cured, liquid silicone composition curable to a rubber, the curable composition loaded with concentrations of 0.5%, 1% and 2% commercially available multi-wall carbon nanotubes.

FIG. 2 is a graphic representation showing electrical resistivity properties of several carbon nanotube silicone rubber composites. Loading of 0.12%, 0.25%, 0.5%, 1.0% and 2.0% of commercially available multi-wall carbon nanotubes was added to a standardized composition of platinum cured liquid silicone rubber given in FIG. 1. Unless stated otherwise, the standard elastomer used in all examples (for convenience and to allow facile comparison of results only, a single composition was used, although not limiting the scope of the invention and presented with all data provided herein) was Shin Etsu X-34-1372, a two part, platinum cured liquid silicone rubber. The nanotubes were multiwall carbon nanotubes manufactured by Hyperion Catalysis and are approximately 4 nm in diameter by 1 micron or less in length.

The resultant electrical resistivity values, measured in Ohms cm, are plotted. The dramatic drop in electrical resistivity with very low loadings of carbon nanotubes is evident. The present invention may incorporate compositions displaying the electrical resistivity properties shown in FIG. 2 for a nanotube sensor, or other compositions, as generically described herein that display sufficient levels of resistance and piezoelectric resistivity as described herein.

Figure 3:
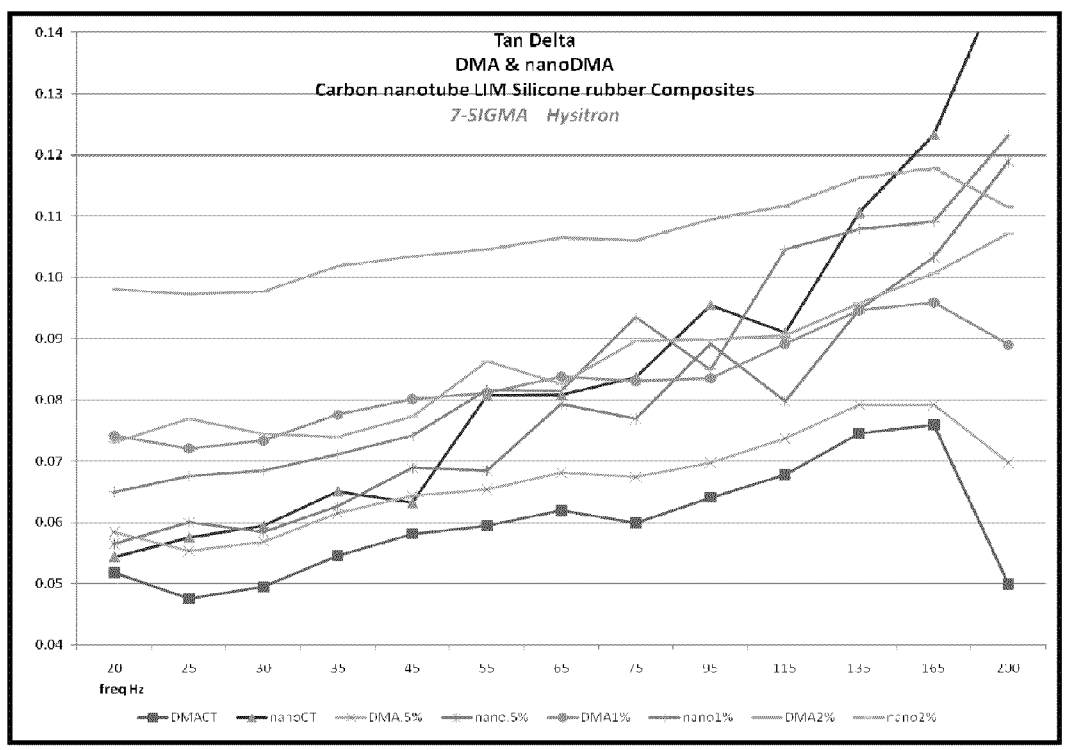
FIG. 3 is a graph of Dynamic Mechanical Analysis (DMA) Tan Delta (ratio between Storage and Loss Modulus) of different CNT loadings, by weight, of silicone rubber composite according to the invention.

FIG. 3 is a graph showing the Dynamic Mechanical Analysis (DMA) Tan Delta (ratio between Storage and Loss Modulus) and nano-DMA testing of a carbon nanotube silicone rubber composite materials as presented in FIG. 1. The DMA plot is Tan Delta which is a ratio of the storage and loss modulus. Also are plotted a conventional DMA test with the nanoDMA testing. Dynamic Mechanical Analysis was carried out by Akron Research & Development Labs using a Visco Analyzer 2000 DMA150 in compression mode. Nanomechanical measurements were performed on a Hysitron TI 900 TriboIndenter™ tester by Hysitron, Inc. The graphically displayed results show the relationship between the DMA and the nano-DMA measurements of a frequency sweep from 20 to 200 hertz, and indicate a correlation of dynamic mechanical properties at the micro and nano levels of performance under strain. The indications are that the low loadings of carbon nanotubes within the general scope of the present invention (e.g., 0.5% to about 3% by total weight of the composition) does not adversely affect the mechanical performance of the material compared to the un-filled base material, thus preserving the physical properties of the chosen base polymer.

Figure 4:
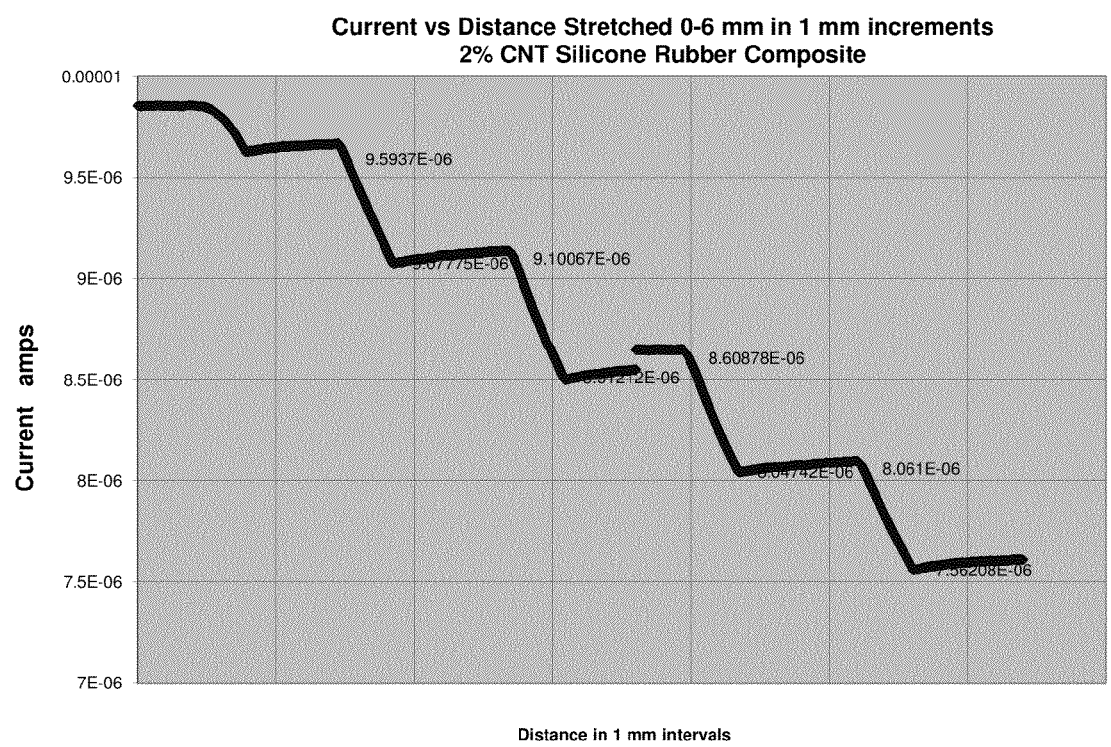
FIG. 4 is a graph of the electrical response of the nanotube sensor under tensile load pulling in 1 mm steps for 6 mm.

FIG. 4 shows the piezoresistive response, measured by the change in current, of a nanotube sensor, composed of material chosen from, but not limited to, FIG. 2 as it is pulled through a series of continuous steps of one millimeter (0.039") in length. The input voltage was 0.1 volt. The increments of distance are clearly discernible, thus providing information on the amount of distance over which a tensile strain is placed upon the sensor.

Figure 5:
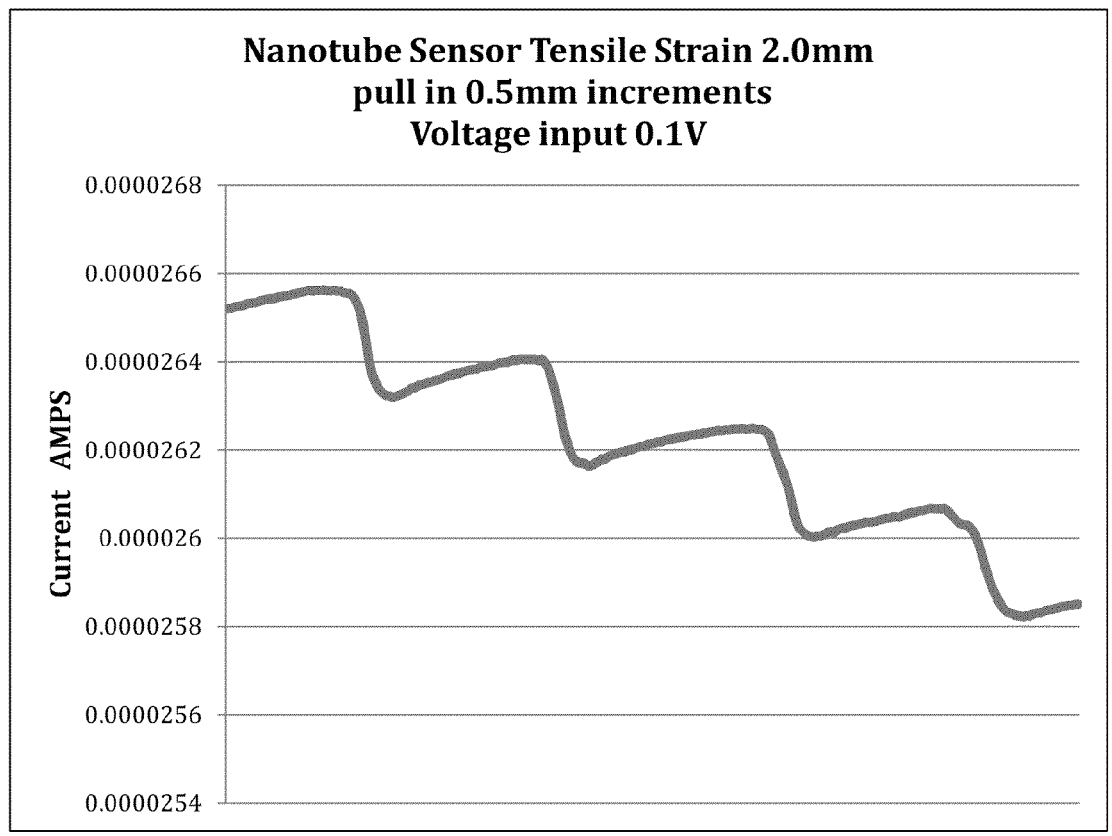
FIG. 5 is a graph of the electrical response of the nanotube sensor under tensile load pulling in 0.5 mm steps for 1 mm.

FIG. 5 shows the piezoresistive response, measured by the change in current, of the nanotube sensor, composed of material chosen from, but not limited to, FIG. 2 as it is pulled through a series of four continuous steps of 0.5 mm for 1 mm in length. The increments of distance clearly show the resolution of the sensor. The input voltage was 0.1 volt.

Figure 6:
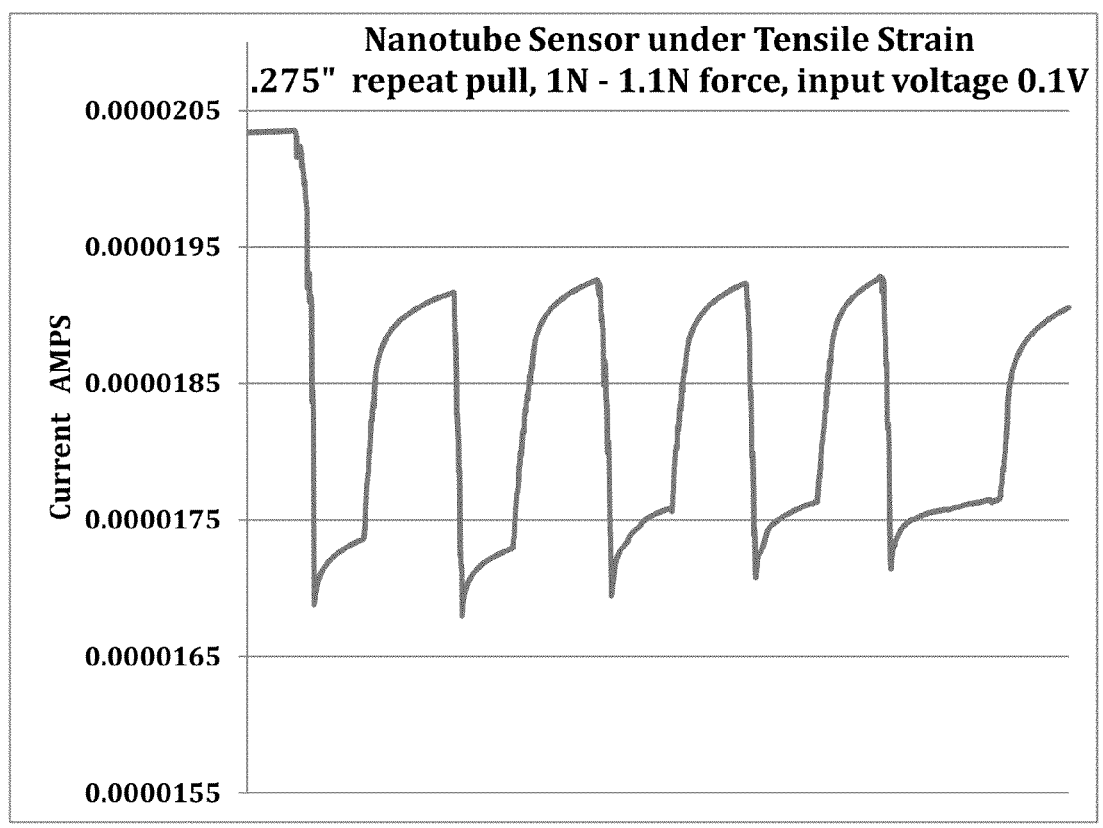
FIG. 6 is a graph of the electrical response of the nanotube sensor under repeated tensile strain.

FIG. 6 shows the change is output current of the sensor, composed of material chosen from, but not limited to, FIG. 2, and attached to a medical mesh fabric device, as it is pulled through a distance and released back to the initial starting point. The repeated tensile strain, of about 1 Newton, and distance pulled of 0.275 inches, shows consistency of repeatability of sensing distance.

Figure 7:
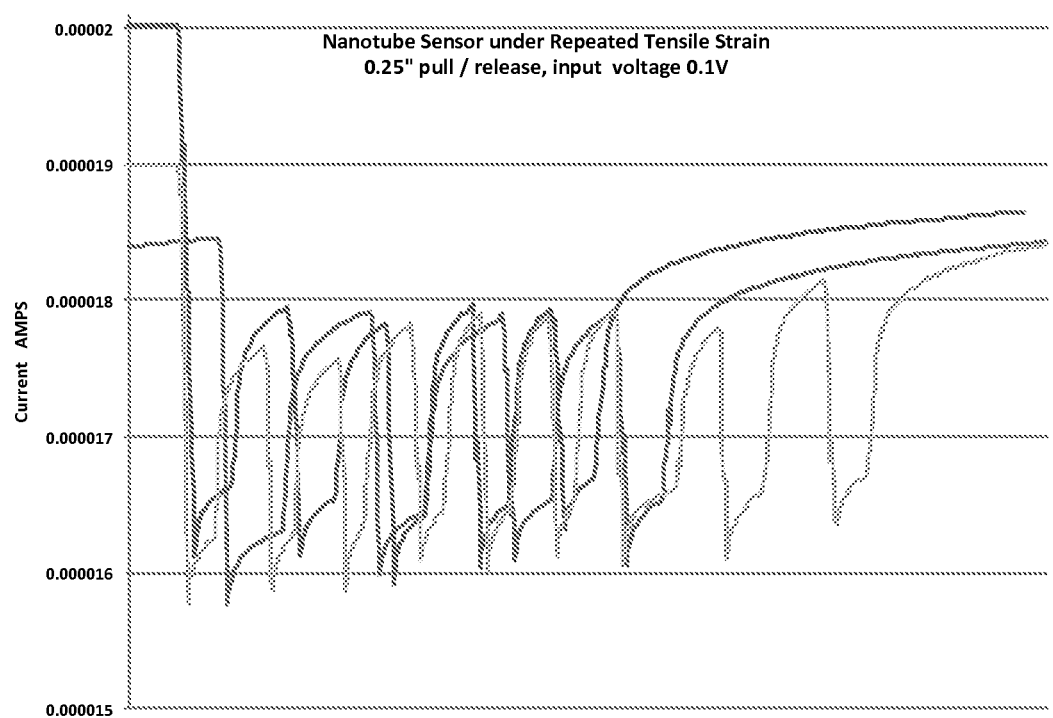
FIG. 7 is a graph of the electrical response of the nanotube sensor under a series of repeated tensile strain.

FIG. 7 shows repeated multiple similar pulls to the sensor of FIG. 6. The dynamic response remains consistent over several periods of elongation.

Figure 8:
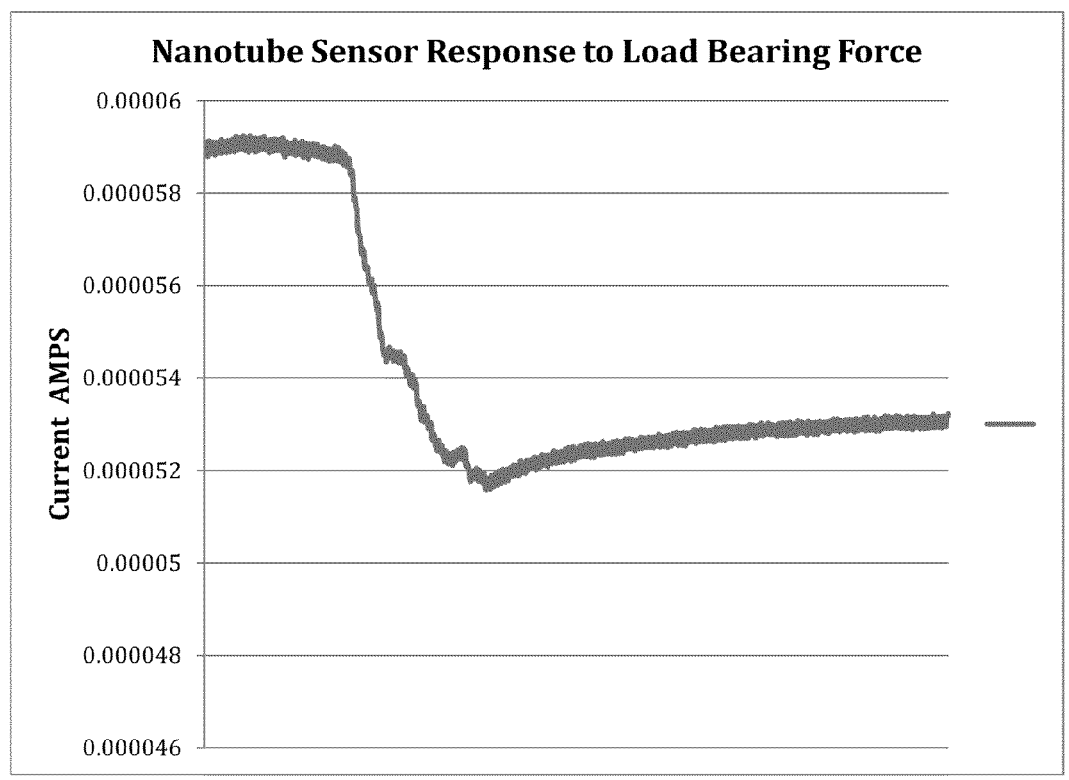
FIG. 8 is a graph of the electrical response of the nanotube sensor under a bearing load.

FIG. 8 shows the piezoresistive response, in terms of current output, of the sensor of FIG. 6 when a bearing load is placed on the sensor.

Figure 9:
FIG. 9 is a side view of an example of one embodiment of a sensor according to aspects of the invention.

FIG. 9 shows an example of embodiment of a sensor within the generic scope of the present invention. FIG. 9 is a side sectional view of an electrically conductive polymer sensor 1 comprising of nanotubes to confer electrical properties. The sensor is comprised of the cured silicone polymer (or equivalent elastomer or flexible polymer). This is a flexible silicone rubber with carbon nanotube uniformly (essentially homogeneously, within the limits of real physical limits on the use of finite material) dispersed within the polymer at a preferred loading of between 0.5% and 3.0%. On each end of material 1 an electrical wire 2 (electrode) and connection 3 which are molded or affixed to the carbon nanotube rubber 1.

Figure 10:
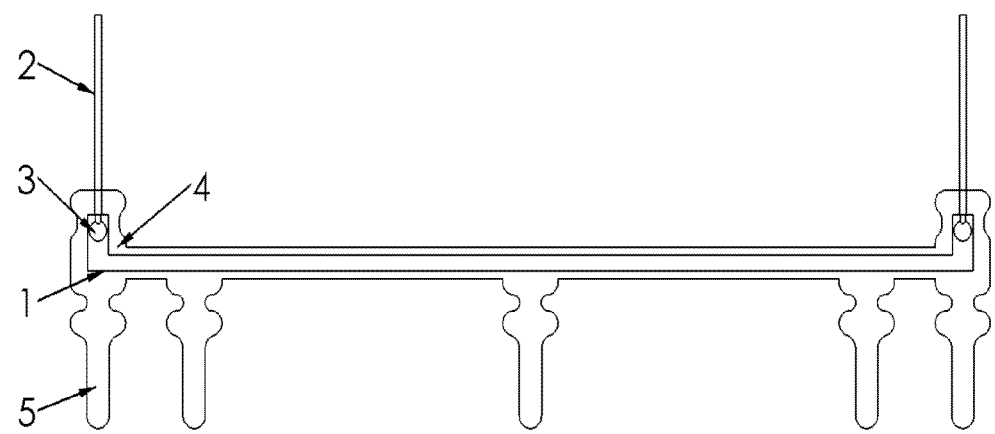
FIG. 10 is a side view of yet another example of one embodiment of a sensor according to aspects of the invention.

FIG. 10 shows yet another embodiment of a sensor within the generic scope of the invention, whereby the carbon nanotube composite rubber 1 with electrical wire 2 and connection 3 are over molded or encased with a non conductive flexible material 4. On the surface of material 4, structures 5 (e.g., posts, snaps, pins, and the like) are molded or otherwise affixed onto the surface for the purpose of attachment to a second body, such as a medical device. The composition of the structures may be the same or different as the composition of the elastomer or polymer of the sensor. Preferably the structure is more rigid to provide more effective securement, and may be comprised of polymer, ceramics, metal or composite materials.

To achieve desired or designed electrical properties to a polymer or elastomer as described herein, such as an epoxy resin, elastomeric polymer or rubber, addition of moderate percentages, such as between 0.5% up to 4% by total weight of the polymer of conductive nanoparticles and especially carbon nanoparticles may be used. Loading with larger conductive particles such as carbon black at levels above 10% by total weight of the composition or total weight of the elastomer, often result in compromised physical properties such as hardness, tensile, thermal and compression. In addition, the electrical conductivity is negatively altered upon large deformations of the material to the point whereby electrical contact between the conducting particles is broken. The addition of very small amounts, even less than 2% by total weight of the composition (as described herein), of carbon nanotubes increases the electrical conductivity of the base material while preserving desired physical properties of the original polymer. The relatively lower loading of carbon nanotubes to a silicone rubber elastomer preserve desired original liquid silicone rubber physical properties such as hardness, tensile, elongation and compression. Low loading, by weight, of carbon nanotubes to a base polymer significantly changes the electrical properties. For example, a 0.5% or 1.0% loading of multi-wall carbon nanotubes dispersed into a liquid polymerizable to a silicone rubber, changes the resistivity of the original silicone rubber elastomer from $10^{13}$ Ωcm to $10^3$ Ωcm, with no significant change in the other important properties of the original properties. Additionally, large deformations of the nanotube composite do not negatively affect the electrical conductance of the material rather the electrical conductivity is maintained.

Also considered within the scope of this disclosure are: types of sensor devices and/or systems used to determine and/or measure strain or pressure The sensors are used to determine and/or measure the amount of pressure or strain applied to an associated surface and used to determine and/or measure tissue thickness, and to determine or measure pressure and/or to provide pressure or strain data to a processor which correlates the pressure data with tissue thickness using a look-up table or other data structure. By knowing the strain or pressure data, a surgeon or technician can then determine the proper alignment of the device before completing the medical procedure.

The processor may be housed in a remotely programmable apparatus which also includes a memory for storing the script programs and the responses to voltage data flow. The remotely programmable apparatus may further include a microprocessor connected to the wires (effectively the communication device from the sensor, with or without a preamplifier), a user interface, and the memory. The microprocessor executes the script programs to identify the strain, communicate the results sets to the practitioner (e.g., through a monitor or printed output or audio signal), receive possible responses to the results of the data (e.g., a signal to readjust the device or reduce the exhibited strain), and transmit the responses to the server and/or monitor through communication networks.

The system may also include wireless communication between the voltage meter reading sensor output and the processor. For example, a microprocessor may be preferably connected to memory using a standard two-wire $I^2C$ interface or using a wireless connection. The microprocessor is also connected to user input buttons to initiate activity, alter readouts requested, respond to signals from the sensor, start a print-out, and the like (as through an I/O port or dedicated printer port, LED, a clock and a display driver. The clock could indicate the current date and time to the microprocessor and measure duration of strain or pressure. The clock may be a separate component, but is preferably built into microprocessor. The display driver operates under the control of microprocessor to display information on a video display or monitor. The microprocessor may be any microprocessor in any format, including a laptop (PC or Mac) and operate on any operating system, including Linux. For example, a PIC 16C65 processor which includes a universal asynchronous receiver transmitter (UART) is an example of a useful processor for communicating with a modem and a device interface. A CMOS switch under the control of the microprocessor alternately connects modem and interface to the UART.

For the purposes of the implementation of the invention, a study was conducted using very low loadings of carbon nanotubes in an elastomeric liquid silicone rubber polymer. The resultant data concluded that desirable electrical properties were conferred to the liquid silicone rubber elastomeric polymer with relatively low, e.g., less than 4% or less than 3%, loadings of multi-walled carbon nanotubes. In addition, the study showed that the desired physical properties were maintained, and that no diluent behavior was observed. Further, the study showed that uniform resistivity was achieved throughout the liquid silicone carbon nanotube rubber composite. These conclusions support the inference that a liquid silicone carbon nanotube rubber composite can be effectively designed as an electrically conductive elastomeric material, while maintaining desirable physical properties such as tensile strength, elongation to break, compression and hardness.

Conventional and nano static and dynamic properties testing of materials, such as tensile, elongation, compression set, Dynamic Mechanical Analysis, surface and volume resistivity, etc., are often used to characterize material properties. Values from these tests are considered in the choice of materials suitable for application in the flexible sensor. Such test were conducted on carbon nanotube liquid silicone rubber composites to evaluate the effect of different loadings of carbon nanotube with different liquid rubbers.

In addition for the purpose of the invention, a study was conducted using very low loading of carbon nanotubes in an elastomeric silicone rubber polymer, measuring the changes in the electrical resistivity of the composite polymer during deformation. The changes in resistivity were measured as a function in the change of the output current of the material with a constant voltage applied to the material. The study compared loadings, by weight, of carbon nanotubes homogeneously mixed in the standard silicone polymers of between 0.5% and 2%. The resultant composites were deformed under various loading conditions and the change in resistivity of the composite monitored. For the purpose of the medical application, the study used voltages of between 0.01 and 1 volts. The study conducted measured large repeated deformations such as tensile strain in the order of 10 mm elongation as well as small deformation in the order of microns. The resultant change in resistivity correlated with the amount of deformation or force applied to the polymer composite.

Another aspect of the present technology includes accurate measurement of the amount of deformation of, strain exhibited on, or pressure exerted upon, a medical device inserted into a patient is determined by utilizing a sensor as described herein attached to the medical device and exhibiting the above described piezoresistive properties that conductive nanotubes confer to an elastic medium. Such a sensor can be used to measure elongation or strain of a medical device during insertion, or immediately after insertion or even long after insertion into the patient. Such a sensor can also measure the deformation or load that is placed upon the medical device by the organ or with the body part with which the medical device is in contact. That measurement may be a direct pressure measurement, or by comparing strain with known degrees of pressure applied perpendicular to the sensor (and using a look-up table). Such a sensor may also be used to measure the amount of pressure that is being applied to a body part by the medical device. Such a sensor may also be used to monitor changes over time of the elongation, deformation, strain, load or pressure of an object or body part to which the sensor is affixed.

The present invention also relates to an electrically conductive rubber whereby the conductive agent applied to a flexible polymer base are carbon nanotubes. The carbon nanotubes loadings are dispersed homogeneously into the polymer base such that the flexibility of the original base polymer is not dramatically compromised, and such that the electrical response of the composite is not significantly compromised (e.g., by more than 15%) over repeated deformations (e.g., over 20 deformations with greater than 100% elongation). A constant voltage is applied to the sensor and the electrical current is monitored at a point some distance from the voltage input through electrical connection with the electrodes or wires on the sensor. As the sensor is deformed, the current will change in response to the deformation due to the change in electrical resistivity of the composite material. For sensing deformation in devices in medical applications, the input voltage may be very low, in the order of less than 1 volt (e.g., 0.05 up to 1 volt), depending upon the electrical conductivity of the composite polymer. For medical applications the nanotube composite may be incased within a flexible polymer to insulate the electrically conductive composite and to comply with FDA regulations that may concern nano particle exposure.

The invention further relates to a sensor for which elongation of the sensor is directly related to the distance that the sensor, or the medical device to which the sensor is affixed, is pulled or compressed. The distance may be a continuous pull or compression or an incremental pull or compression of the sensor. The change in resistivity of the nanotube composite sensor directly correlates to the change in distance that the sensor is pulled or compressed. The change in resistivity may be measured directly as a change in resistance or as the change in current when a constant voltage is applied. Additionally, the load placed upon the sensor, or the medical device to which it is affixed, can be determined likewise by the change in resistivity of the nanotube composite sensor.

Various other aspects of the invention also relate to a flexible electrically conductive nanotube silicone rubber composite that is contained within a non electrically conductive medical grade silicone rubber, for the express purpose of distance, compression or load measurement by observing the change in electrically resistivity of the nanotube composite. The attaching element can be used to attach the sensor directly to other sensors or devices attached to a medical patient for the purpose of measuring the stress or strain or other applied forces to the device. Additionally a sensor is described having at least an elastic body containing conductive nanotubes homogeneously distributed therein, the sensor contained or attached to or within an elastic body not containing conductive nanotubes and not electrically conductive, of which at least one surface of the sensor with physical attaching element thereon. Where embedded in another material, the attaching members assure elongation along with the embedding body.

Another aspect of the technology includes a sensor comprising of an elastic body comprised of a silicone rubber containing a loading of between 0.5% and 3%, by wt. of conductive nanotubes such as carbon nanotubes, homogeneously distributed therein, with electrodes adhered to or molded within the nanotube composite for the purpose of applying an electrical current through the composite and a detection system that detects absolute amounts of voltage and/or changes in voltage across the electrodes.

A further aspect of the present technology may include a sensor having an elastic body comprised of a liquid silicone rubber containing a loading of between 0.5% and 3%, by wt. of carbon nanotubes, homogeneously distributed therein, with electrodes adhered to or molded with the nanotube composite and contained entirely within a medical grade non conductive flexible silicone rubber.

Another aspect of the present invention may include an electrically conductive silicone rubber composite comprised of a liquid silicone rubber with a multi-wall carbon nanotube loading of between 1%-3% by weight and a hardness between 10 and 60 Asker C hardness.

An electrically conductive silicone rubber composite comprised of a liquid silicone rubber with a multi-wall carbon nanotube loading of between 0.5%-3% by weight, a hardness of between 10 and 60 Asker C and elongation property greater than 200%.

An electrically conductive silicone rubber composite comprised of a liquid silicone rubber with a multi-wall carbon nanotube loading of between 1%-3% by weight, a hardness of between 10 and 60 Asker C, an elongation property greater than 200% and electrical resistivity of $10^3$ Ohm/sq or less.

Although specific dimensions, compositions, voltages, materials and fields of use are described herein, it must be understood that these are examples enabling the generic scope of the invention and should not limit the scope of enforcement of claims herein.

The invention claimed is:

1. A method of sensing dimensional changes, stress changes or pressure changes on a substrate attached to body parts within a patient's body comprising: temporarily and non-destructively attaching a piezoresistant sensor to a surface attached to a patient's body, the piezoresistant sensor comprising an electrically conductive elastic body having at least one pair of opposed ends, and the elastic body consisting essentially of a single layer conductive nanotubes homogeneously distributed therein, the elastic body having at least one surface with two opposed ends and electrodes at each of the opposed ends of the single layer, passing a current through the elastic body between the two electrodes while within the patient's body, sensing the current passing through the elastic body only through the single layer, performing a mechanical step on the substrate that causes stress, strain or elongation on the conductive elastic body while within the patient's body, and measuring changes in the current between the electrodes on only the single layer.

2. The method of claim 1 wherein the conductive elastic body comprises from 0.02% to 8% by total weight of homogeneously dispersed conductive nanotubes.

3. The method of claim 1 wherein the elastic body comprises an elastomeric polymer which is comprised of a platinum-cured liquid silicone rubber composite having a hardness of between 10 and 60 Asker C and elastic elongation capability of at least 200% and the elastic body is elongated at least 200%.

4. The method of claim 1 wherein the elastic body comprises an elastomeric polymer which is comprised of a platinum-cured liquid silicone rubber composite having a hardness of between 10 and 60 Asker C and elastic elongation capability of at least 200% and the elastic body is elongated at least 100%.

5. The method of claim 2 wherein the elastic body is elongated at least 100% and the electrical response of the composite is not compromised by more than 15%.

6. The method of claim 2 wherein measured changes in current between the electrodes is related by execution of code in a processor to a pressure, stress level or change in dimension of the conductive elastic body during performing of the mechanical step.

7. The method of claim 6 wherein after measured changes in current have been identified, removing the sensor from the substrate.

8. The method of claim 7 wherein the sensor is detached from the substrate from attachment by hooks, pins or post grasping a mesh surface of the substrate.

9. The method of claim 8 wherein the substrate comprises a mesh to support tissue, and the mechanical step performed is planting the mesh into a patient to support tissue.

* * * * *